(12) United States Patent
Cummings et al.

(10) Patent No.: US 6,773,678 B2
(45) Date of Patent: Aug. 10, 2004

(54) MOUNTING SYSTEM AND RETRACTABLE SENSOR HOLDER FOR ANALYTICAL SENSORS

(75) Inventors: Donald D. Cummings, Greenwood, IN (US); Geoffrey W. Wickens, Greenwood, IN (US); R. Todd Lucey, Fishers, IN (US); Todd M. Hockemeyer, Fishers, IN (US)

(73) Assignee: Endress + Hauser Conducta Gesellschaft fur Mess und Regeltechnik mbH + Co., Gerlingen (DE)

( * ) Notice: Subject to any disclaimer, the term of this patent is extended or adjusted under 35 U.S.C. 154(b) by 344 days.

(21) Appl. No.: 09/804,000

(22) Filed: Mar. 12, 2001

(65) Prior Publication Data

US 2001/0028865 A1 Oct. 11, 2001

Related U.S. Application Data

(60) Provisional application No. 60/190,845, filed on Mar. 20, 2000.

(51) Int. Cl.[7] ................................................. B01L 9/00
(52) U.S. Cl. ....................... 422/104; 422/68.1; 436/165
(58) Field of Search ................................. 436/164, 165, 436/43; 422/62, 68.1, 83, 104, 103

(56) References Cited

U.S. PATENT DOCUMENTS

| | | |
|---|---|---|
| 3,545,721 A | 12/1970 | Shafer |
| 3,578,289 A | 5/1971 | Chancenay et al. |
| 3,581,569 A | 6/1971 | Black |
| 3,582,042 A | 6/1971 | Grenier |
| 3,599,933 A | 8/1971 | Piccardo |
| 3,603,560 A | 9/1971 | Merrill et al. |
| 3,628,915 A | 12/1971 | Robertson |
| 3,656,713 A | 4/1972 | Walton |
| 3,674,238 A | 7/1972 | Pickles et al. |

(List continued on next page.)

FOREIGN PATENT DOCUMENTS

| | | |
|---|---|---|
| EP | 0 006 277 | 1/1980 |
| EP | 0 136 797 | 4/1985 |
| EP | 0 142 862 | 5/1985 |
| EP | 0151285 | 8/1985 |
| EP | 0 553 939 | 5/1986 |
| EP | 0 206 451 | 12/1986 |
| EP | 0 235 274 | 3/1987 |
| EP | 0278341 | 8/1988 |
| EP | 0 299 703 | 1/1989 |

(List continued on next page.)

OTHER PUBLICATIONS

Sterlizable pH Electrode Holder CPA 465 Technical Information TI 14C/24/ae/01.99, Endress + Hauser, no date supplied.
InTrac® 777–SL Retractable Housing For In–Line pH or ORP Measurement, Mettler Toledo © 10/88.
Naconnect™ The Flush Mounted Sanitary Connector, Nov Aseptic America, Edition 2 9502, no date supplied.

Primary Examiner—Lyle A. Alexander
(74) Attorney, Agent, or Firm—Bose McKinney & Evans LLP

(57) ABSTRACT

An apparatus for holding a sensor for sensing the contents of a vessel is provided. The apparatus has an extended position where the sensor is exposed to the contents and a retracted position for cleaning the sensor. The apparatus includes a process connection configured to connect the apparatus to the wall of the vessel. The process connection defines an aperture including a first rim, a second rim angularly displaced from the first rim, and a sidewall extending between the first rim and the second rim. The sidewall is angularly displaced from the first rim by no less than 135 degrees.

19 Claims, 4 Drawing Sheets

U.S. PATENT DOCUMENTS

| | | |
|---|---|---|
| 3,691,846 A | 9/1972 | Ingold |
| 3,737,145 A | 6/1973 | Heller et al. |
| 3,744,755 A | 7/1973 | Gary, Jr. et al. |
| 3,746,814 A | 7/1973 | Lackey et al. |
| 3,750,650 A | 8/1973 | Ruttgers |
| 3,779,513 A | 12/1973 | Levine |
| 3,780,985 A | 12/1973 | Perry |
| 3,782,686 A | 1/1974 | Cowie |
| 3,792,835 A | 2/1974 | Shafer |
| 3,794,297 A | 2/1974 | Duer et al. |
| 3,806,087 A | 4/1974 | Hulslander |
| 3,807,691 A | 4/1974 | Barley |
| 3,813,938 A | 6/1974 | Grosch et al. |
| 3,815,870 A | 6/1974 | Milleville et al. |
| 3,819,149 A | 6/1974 | Kinder |
| 3,819,159 A | 6/1974 | Swatman et al. |
| 3,850,039 A | 11/1974 | Brakebill |
| 3,919,515 A | 11/1975 | Bangs |
| 3,950,632 A | 4/1976 | Rivelli |
| 3,974,869 A | 8/1976 | Abe et al. |
| 4,014,512 A | 3/1977 | Cheever et al. |
| 4,033,170 A | 7/1977 | Kawamura et al. |
| 4,036,470 A | 7/1977 | Illing |
| 4,045,642 A | 8/1977 | Driscoll |
| 4,055,324 A | 10/1977 | Hughes et al. |
| 4,055,722 A | 10/1977 | Lukyanov et al. |
| 4,150,810 A | 4/1979 | Laignel et al. |
| 4,151,577 A | 4/1979 | Yavnieli et al. |
| 4,173,328 A | 11/1979 | Karbo |
| 4,180,244 A | 12/1979 | Rosenitsch |
| 4,182,927 A | 1/1980 | Phillips |
| 4,193,580 A | 3/1980 | Norris et al. |
| 4,198,279 A | 4/1980 | Brown et al. |
| 4,222,391 A | 9/1980 | Rawson et al. |
| 4,224,566 A | 9/1980 | Bakale et al. |
| 4,233,619 A | 11/1980 | Webb et al. |
| 4,262,200 A | 4/1981 | Guy |
| 4,264,424 A | 4/1981 | Niedrach |
| 4,270,731 A | 6/1981 | Jackson |
| 4,272,056 A | 6/1981 | Komamura et al. |
| 4,294,591 A | 10/1981 | Kahl |
| 4,300,340 A | 11/1981 | Pozzo |
| 4,309,506 A | 1/1982 | Squires |
| 4,315,990 A | 2/1982 | Sheets |
| 4,319,138 A | 3/1982 | Sweet |
| 4,339,110 A | 7/1982 | Ortega |
| 4,342,878 A | 8/1982 | Wilson, II et al. |
| 4,346,864 A | 8/1982 | Feller |
| 4,385,391 A | 5/1983 | Hillers et al. |
| 4,393,565 A | 7/1983 | Wilson, II et al. |
| 4,395,613 A | 7/1983 | Barr et al. |
| 4,397,446 A | 8/1983 | Jelinek |
| 4,434,496 A | 2/1984 | Krogsrud |
| 4,446,561 A | 5/1984 | Zöllner et al. |
| 4,478,388 A | 10/1984 | George |
| 4,494,730 A | 1/1985 | George |
| 4,507,973 A | 4/1985 | Barr et al. |
| 4,540,156 A | 9/1985 | Cross |
| 4,590,425 A | 5/1986 | Schonstedt |
| 4,595,487 A | 6/1986 | Nunlist |
| 4,632,018 A | 12/1986 | Lymburner |
| 4,640,820 A | 2/1987 | Cooper |
| 4,659,993 A | 4/1987 | Womack |
| 4,668,216 A | 5/1987 | Martin et al. |
| 4,679,431 A | 7/1987 | Jacob et al. |
| 4,695,164 A | 9/1987 | Zivitz et al. |
| 4,697,786 A | 10/1987 | Kennedy |
| 4,703,664 A | 11/1987 | Kirkpatrick et al. |
| 4,717,803 A | 1/1988 | Alexandersson |
| 4,745,742 A | 5/1988 | Nada et al. |
| 4,773,626 A | 9/1988 | Rohlfing et al. |
| 4,777,342 A | 10/1988 | Hafner |
| 4,778,538 A | 10/1988 | Lyman |
| 4,815,470 A | 3/1989 | Curtis et al. |
| 4,829,818 A | 5/1989 | Bohrer |
| 4,856,514 A | 8/1989 | Rabinowitz et al. |
| 4,860,603 A | 8/1989 | Russoniello |
| 4,860,983 A | 8/1989 | Akiba |
| 4,864,724 A | 9/1989 | Bergstrom |
| 4,870,242 A | 9/1989 | Sebzda, Sr. |
| 4,875,359 A | 10/1989 | Akiba |
| 4,879,903 A | 11/1989 | Ramsey et al. |
| 4,895,031 A | 1/1990 | Cage |
| 4,898,035 A | 2/1990 | Yajima et al. |
| 4,914,966 A | 4/1990 | White, Jr. et al. |
| 4,924,051 A | 5/1990 | Sebzda, Sr. |
| 4,937,912 A | 7/1990 | Kurz |
| 4,942,764 A | 7/1990 | Dews et al. |
| 4,943,210 A | 7/1990 | Bailey, Jr. et al. |
| 4,958,056 A | 9/1990 | Tomac |
| 4,986,123 A | 1/1991 | Lösing et al. |
| 4,988,077 A | 1/1991 | Conley et al. |
| 4,989,783 A | 2/1991 | Douglas |
| 5,030,830 A | 7/1991 | Okada |
| 5,055,650 A | 10/1991 | Barthes et al. |
| 5,065,892 A | 11/1991 | Lukez |
| 5,070,249 A | 12/1991 | White |
| 5,076,541 A | 12/1991 | Daghe et al. |
| 5,086,650 A | 2/1992 | Harrington et al. |
| 5,088,690 A | 2/1992 | Stellmacher et al. |
| 5,100,103 A | 3/1992 | Conley et al. |
| 5,142,908 A | 9/1992 | Chamblin, Sr. et al. |
| 5,149,054 A | 9/1992 | Passerell et al. |
| 5,152,372 A | 10/1992 | Volman |
| 5,154,396 A | 10/1992 | Conley et al. |
| 5,173,922 A | 12/1992 | Arakawa et al. |
| 5,186,433 A | 2/1993 | Pausch |
| 5,192,425 A | 3/1993 | Cyphers et al. |
| 5,199,308 A | 4/1993 | Lawhon et al. |
| 5,201,222 A | 4/1993 | Johnson |
| 5,219,149 A | 6/1993 | Combeau |
| 5,228,649 A | 7/1993 | Szewczyk et al. |
| D337,959 S | 8/1993 | Lawhon et al. |
| 5,239,155 A | 8/1993 | Olsson |
| 5,251,470 A | 10/1993 | Lampe et al. |
| 5,259,219 A | 11/1993 | Dausch et al. |
| 5,267,470 A | 12/1993 | Cook |
| 5,285,154 A | 2/1994 | Burreson |
| 5,305,988 A | 4/1994 | Cox |
| 5,306,236 A | 4/1994 | Blumenfeld et al. |
| 5,311,785 A | 5/1994 | Bar-Shay |
| 5,312,086 A | 5/1994 | Hollingworth |
| 5,315,563 A | 5/1994 | Lichtenfels, II et al. |
| 5,341,661 A | 8/1994 | Dausch et al. |
| 5,342,126 A | 8/1994 | Heston et al. |
| D350,297 S | 9/1994 | Weisel |
| 5,347,872 A | 9/1994 | Clark |
| 5,355,726 A | 10/1994 | Zurek et al. |
| 5,369,990 A | 12/1994 | Zurek et al. |
| 5,379,658 A | 1/1995 | Lihtenfels, II et al. |
| 5,386,432 A | 1/1995 | Ficalora et al. |
| 5,402,983 A | 4/1995 | Bernhardt |
| 5,452,608 A | 9/1995 | Green |
| 5,453,688 A | 9/1995 | Cecco et al. |
| 5,466,422 A | 11/1995 | von Leeuwen |
| 5,480,124 A | 1/1996 | Bartlett et al. |
| 5,505,073 A | 4/1996 | Gerblinger et al. |
| 5,527,335 A | 6/1996 | Bolduc et al. |
| 5,550,478 A | 8/1996 | Kopera |
| 5,552,771 A | 9/1996 | Leyden et al. |
| 5,563,340 A | 10/1996 | Clowater et al. |

| | | | | | | |
|---|---|---|---|---|---|---|
| 5,596,147 | A | 1/1997 | Wilda et al. | EP | 0327936 | 8/1989 |
| 5,600,998 | A | 2/1997 | Dean, Jr. | EP | 0 336 931 | 10/1989 |
| 5,612,497 | A | 3/1997 | Walter et al. | EP | 0413232 | 2/1991 |
| 5,636,634 | A | 6/1997 | Kordis et al. | EP | 0 448 686 | 10/1991 |
| 5,644,093 | A | 7/1997 | Wright et al. | EP | 0449694 | 10/1991 |
| 5,652,488 | A | 7/1997 | Rennau | EP | 0 462 998 | 1/1992 |
| 5,665,920 | A | 9/1997 | Martin | EP | 0533303 | 3/1993 |
| 5,709,474 | A | 1/1998 | Richardson et al. | EP | 0545177 | 6/1993 |
| 5,719,342 | A | 2/1998 | Borchers et al. | EP | 0 542 959 | 11/1993 |
| 5,728,289 | A | 3/1998 | Kirchnavy et al. | EP | 0 572 010 | 12/1993 |
| 5,743,646 | A | 4/1998 | O'Connell et al. | EP | 0 634 637 | 1/1995 |
| 5,744,697 | A | 4/1998 | Martell et al. | EP | 0 654 141 | 5/1995 |
| 5,829,880 | A | 11/1998 | Dietrich | EP | 0 672 239 | 9/1995 |
| 5,833,214 | A | 11/1998 | Kunsmann | EP | 067211 | 12/1995 |
| 5,858,224 | A | 1/1999 | Schwandt et al. | EP | 0 735 349 | 10/1996 |
| 5,881,996 | A | 3/1999 | Walsh, Jr. et al. | EP | 0 737 847 | 10/1996 |
| 5,890,699 | A | 4/1999 | Sugihara et al. | EP | 0 774 652 | 5/1997 |
| 5,893,977 | A | 4/1999 | Pucci | EP | 0 777 116 | 6/1997 |
| 5,901,945 | A | 5/1999 | Schalk | EP | 0796984 | 9/1997 |
| 5,918,834 | A | 7/1999 | Sommer et al. | EP | 0 834 727 | 4/1998 |

FOREIGN PATENT DOCUMENTS

| | | | |
|---|---|---|---|
| EP | 0893643 | 1/1999 |
| EP | 0 310 975 | 4/1989 | |
| EP | 0 894 983 | 2/1999 |
| EP | 0 312 329 | 4/1989 | |
| WO | WO 97/14369 | 4/1997 |
| EP | 0 313 262 | 4/1989 | |
| WO | WO 99/26053 | 5/1999 |

MOUNTING SYSTEM AND RETRACTABLE SENSOR HOLDER FOR ANALYTICAL SENSORS

CROSS-REFERENCES TO RELATED APPLICATIONS

This application claims priority from U.S. Provisional Patent Application No. 60/190,845, entitled "A Mounting System and Retractable Sensor Holder for Analytical Sensors," filed Mar. 20, 2000, the disclosure of which is incorporated herein by reference for all purposes.

FIELD OF THE INVENTION

The present invention relates to a retractable sensor holder for immersion-type and flow-type measuring systems, and in particular to a retractable sensor holder that provides an effective cleaning and/or sterilization path for wetted parts of the sensor and sensor holder, while providing substantially flush mounting with the vessel wall.

BACKGROUND OF THE INVENTION

The pharmaceutical and biotechnology markets employ sensitive processes that require analytical sensors to be mounted in sterile environments. Typically, these environments are closed vessels, wherein fermentation and cell growth cycles can last from a few days to several months. The analytical sensors, for example pH sensors, are sensitive devices that can be affected by the conditions experienced inside the vessels, and must be maintained correctly to ensure adequate performance. Fouling from proteins will cause drift and biomass penetrating the electrode reference system will over time cause some offsets. Harsh cleaning cycles that would otherwise destroy pH electrodes require users to manually remove them prior to commencing with vessel cleaning.

Conformance to specific industry standards is often required to ensure the proper cleaning and sterilization of the vessels and the sensors. For example, ASME Bioprocessing standard 1997 & 3-A recommendations ("the 3A Standards"), which are incorporated herein by reference for all purposes, have been developed by/for producers of meat, milk and eggs and are still the standards by which most food and beverage producers gage their equipment for suitability. Meat, milk and eggs are considered to be "worst case" for bacterial growth. If equipment follows the standards for these products, then producers properly using the equipment can be assured that the equipment will not add to their bacterial problems. Producers of other foods with less bacterial risk may thus choose how much of the standards to employ based upon what they feel they need. However, some users may ask for even further requirements, such as better surface finishes, etc.

In general, the 3A Standards assume that equipment will meet sanitation requirements by at least one of two methods (even though some users will demand both): "mechanical cleaning" (often called by users as "clean-in-place" or "CIP"), and "removable for cleaning." In the latter case, equipment must be easily removable (i.e., require no tools to remove) so that an operator or quality assurance or regulatory inspector can routinely pull out sensors, inspect them for cleanliness, and clean them if necessary, before re-inserting them into the process. In the case of mechanical cleaning, the idea is that procedures carried out within the process itself can clean the installed sensors—with no need to pull them out. In general, this method requires such things as very smooth surface finishes and no acute angle corners (e.g., angles no less than 135 degrees) where material can build up or where flowing cleaning fluids cannot carry buildup away. Further, using the mechanical cleaning method, the equipment must be able to withstand the process and protect the integrity of the sealed, cleaned process system. For example, it is routine after a food or fermentation batch to clean the system before starting a new batch of similar or different product. To this end, a typical method might be to follow a product batch with hot water, then a caustic solution, then hot water, then a steam-sterilization, and then let the sealed system cool down (which creates a vacuum situation).

Regardless of which method is employed, under the 3A Standards anytime a "seal" is exposed to the process it must be an O-ring (i.e., not a flat gasket) that is acceptable for contact with food and it must be removable/replaceable by the operator each time the sensor is removed/replaced. Furthermore, all other materials of construction must be acceptable for contact with food, normally stainless steel (300 series or better) or TEFLON™. FDA approved food contact materials are listed in Title 21 of the United States Code of Federal Regulations ("21 CFR"), which is incorporated herein by reference for all purposes. Additionally, ASME BPE1997, which is also incorporated herein by reference for all purposes, sets out requirements for easy to clean tank and process connections. It is also noted that there are alternative sanitary standards being developed which seek not to assume cleanliness based upon theoretical design guidelines like the 3A Standards, but rather to actually test equipment with introduction of bacteria and media, cleaning, retesting, etc.

FIG. 1 shows a typical prior art 25 mm process connection or weld spud 1. The historical approach to meeting the various sanitary requirements has become known as the 25 mm side port coupling or 25 mm weld spud, and is commonly used today for pH and dissolved oxygen sensors. The 25 mm weld spud 1 is generally tubularly shaped. In this approach, a "stationary" sensor (not shown) is mounted to a tank wall 2 via the 25 mm weld spud 1. The sensor is held in place within the 25 mm weld spud 1 by a thread coupling 4. The sensor is outfitted with an O-ring that forms a fluid tight seal between the sensor and the inside of the 25 mm weld spud 1. With the sensor mounted in the 25 mm weld spud 1, the sensor will typically be steam sterilized at the same time as the inside of the tank. When maintenance is required, the sensor can be removed from the port by disengaging the quick disconnect fitting or unscrewing the coupling nut, respectively. After the sensor is removed, it can then be cleaned and recalibrated or replaced, if necessary. Once maintenance is completed, the sensor is returned to the 25 mm weld spud 1. The entire tank then undergoes sterilization to ensure that no foreign organisms were inadvertently introduced during the sensor maintenance. However, this approach has some obvious limitations, including: (1) maintenance can only be carried out while the vessel is empty; (2) sensors must be handled and maintained manually; and (3) after maintenance the entire tank needs to be re-sterilized. Moreover, because the generally tubular 25 mm weld spud 1 extends away from the inside of the tank, the interior 3 of the 25 mm weld spud 1 cannot be adequately reached by steam for sterilization and for cleaning.

In order to provide more flexibility to users, the concept of "retractable" sensor holders emerged some years ago. The idea was to be able to retract the sensor from the vessel and isolate it from the tank without having to interrupt the process. Maintenance could then be carried out on the sensor while the process continued to run. The object has been to design retractable holders that would fit onto the existing process connections. To this end, many unsuccessful attempts have been made to use the de facto standard 25 mm weld spud in conjunction with sanitary retractable holders. These too have not been successful primarily because not all wetted parts can be adequately reached by steam for sterilization. For example, FIG. 2 shows a typical prior art retractable holder 12 in a retracted, cleaning position.

The retractable holder 12 includes a stationary portion 5 and a movable portion 6 which holds a sensor 14. The stationary portion 5 is connected to a vessel 16 (such as, for example, a tank) by a 25 mm weld spud 18. In the retracted position, a front cap 20 provides a substantially flush mount with the inside surface 26 of the vessel 16, and isolates the inside of the retractable holder 12 and the sensor 14 from the inside of the vessel 16. A cleaner inlet 22 and a cleaner outlet 24 are provided in the retractable holder 12 to introduce cleaning and/or sterilization agents to clean the sensor 14 and the interior of the retractable holder 12. A pair of O-rings 8, 10 are placed between the stationary portion 5 and the movable portion 6 to provide a fluid tight seal. The design provides a substantially flush, cleanable mount with the inside surface 26 of the vessel 16 that facilitates vessel cleaning. However, the cleaning of the sensor 14 and the interior of the holder 12 is still problematic. First, the area between the two O-rings 8, 10 cannot be effectively reached during the cleaning process. Also, the diameters of analytical sensors, for example pH electrode sensors, can typically be 12 mm and the inside diameter of the port adapter is only 25 mm. During cleaning, all internal surfaces and seals must be adequately contacted by cleaning agent with sufficient velocity. But channel 28 (the space between the stationary part and the moving part of the retractable holder 12) is impracticably narrow. The cleaning agent takes the path of least resistance and flows between the inlet 22 and the outlet 24 with insufficient velocity of the cleaner in the channel 28. The end result is poor cleaning of the sensor 14 and the area immediately behind the front cap 20. During sterilization, for example with steam, the same problems are evident. Steam sterilization is typically performed at 120–130° C. for approximately one hour. With steam, the situation is further complicated because steam condensate can become trapped in the area immediately behind the front cap 20, making it difficult to raise the chamber temperature to the required level for effective sterilization.

Alternative designs have been attempted to solve some of the foregoing problems, for example the INTRAC® brand 777-SL Retractable Housing from Mettler-Toledo Process Analytical, Inc. of Wilmington, Mass. This retractable housing has a similar design based on 25 mm port couplings and O-rings, but it differs in that the sensor shaft is retracted further back into the chamber and it has multiple inlets and outlets for cleaning and sterilization agents. However, information from independent tests show that while drainability of steam condensate was better, the interior chamber of the retractable holder could still not be effectively sterilized or cleaned. Moreover, this retractable holder does not provide a flush in-vessel surface with the inside surface of the vessel to facilitate vessel cleaning.

Another alternative design is to use a retractable holder which requires a process connection that is much wider than the defacto standard 25 mm port connection, for example, the Endress+Hauser type CPA465-F retractable holder ("CPA465-F"). The CPA465-F provides enough room for all internal surfaces of the chamber and the process wetted sensor shaft to be adequately reached for cleaning and sterilization. The wider body process connection allows steam and cleaning agents to reach all the way down to the sensor and the back of the probe seal. Up to this point the CPA465-F has been available with industry standard process connections including the 2 inch TRI-CLAMP™, APV™ and VARIVENT™ quick disconnect type fittings (see Endress+Hauser Technical literature TI 146 C/24/ae). These process connections are most ideally suited to pipeline type installation. The manufacturers of the APV™ and VARIVENT™ fittings have also developed sanitary design flow through chambers for use with their process connections. However, most applications require the sensor to be mounted onto a vessel wall (typically fermenters and reactor vessels). In order to mount the CPA465-F to a vessel wall using the TRI-CLAMP™, APV™ or VARIVENT™ process connections, a nozzle would have to be welded to the side of the vessel at an angle. This is not considered preferred practice for sanitary applications as such nozzles cannot be cleaned easily and disturb the laminar flow often required for ideal mixing within the vessels. A flush mount construction approach is preferred.

Thus, there is a need for a retractable holder and process connection that has an effective cleaning and/or sterilization path for wetted parts of the sensor and retractable holder while also being capable of a substantially flush mounting with the interior wall of a vessel for cleaning and/or sterilization of the interior surface of the vessel.

SUMMARY OF THE INVENTION

In one embodiment, the present invention provides an apparatus for holding a sensor for sensing the contents of a vessel that has a wall. The apparatus has an extended position where the sensor is exposed to the contents of the vessel and a retracted position for cleaning and/or sterilization of the sensor. The apparatus includes a process connection configured to connect the apparatus to the wall of the vessel. The process connection defines an aperture including a first rim, a second rim angularly displaced from the first rim, and a sidewall extending between the first rim and the second rim. The sidewall is angularly displaced from the first rim by no less than 135 degrees.

In an alternative embodiment, the present invention provides a process connection for connecting a sensor holder to an opening in a wall of a vessel. The process connection includes a connector configured to be coupled to the sensor holder and further configured to be coupled to the wall of the vessel. The connector defines an aperture including a first rim, a second rim angularly displaced from the first rim, and a sidewall extending between the first rim and the second rim. The sidewall is angularly displaced from the first rim by no less than 135 degrees.

The retractable holder and process connection of the present invention incorporate the advantages of the wide body retractable holder with the benefits of a substantially flush mount process connection. In addition, it improves calibration accuracy via improved flow through the "cleaning" chamber, which also sometimes functions as a calibration chamber. The more complete ingress of calibration fluids (buffers), as well as proper rinsing out of other fluids (buffers of different pH value) prior to calibration improves calibration. Further it facilitates better rinse out/blow out of fluids prior to re-introducing the sensor to the process. This results in a retractable holder that provides repeatable and effective cleaning and/or sterilization of the sensor and the holder, while also providing for effective cleaning and/or sterilization of the vessel.

The retractable holder and process connection of the present invention addresses the requirements for sanitary operation. It has a retractable design that can be moved between an extended measuring position and a retracted, cleaning position either manually or automatically. It provides a steam sterilizable chamber containing the sensor when the retractable holder is in the retracted, cleaning position. It provides a substantially flush process connection with the interior of the vessel providing a cleanable process connection on the interior of the vessel.

The holder enables a sensor, for example a pH, ORP, Conductivity, Turbidity or Dissolved oxygen sensor, to be manually or automatically retracted from a sanitary vessel, to be serviced (cleaned/buffered) or replaced. The new or serviced sensor can then be effectively steam sterilized and be re-inserted into the vessel without contaminating the vessel. The process connection is optimally designed to facilitate its ease of cleaning and sterilization so that the process wetted components of the holder can be effectively cleaned and steamed in place while the vessel is undergoing clean-in-place and sterilization-in-place cycles.

These features, among others, make the present invention a viable solution for users who are looking for a product that allows sensors to be inserted (manually or automatically) into a sterile environment (without contamination occurring), while providing a process connection that is also easily cleaned and sterilized from the tank side. No hard to clean nozzles are needed that will disturb the laminar flow profile within tank. The flush connection ensures that the full stroke of the holder is available for insertion into the tank away from possible skin effects that may cause un-homogeneous samples.

Additional objects, advantages and novel features of the invention are set forth in the description that follows, and will become apparent to those skilled in the art upon reviewing the drawings and the following description.

DESCRIPTION OF THE PREFERRED EMBODIMENT

Figure 1:
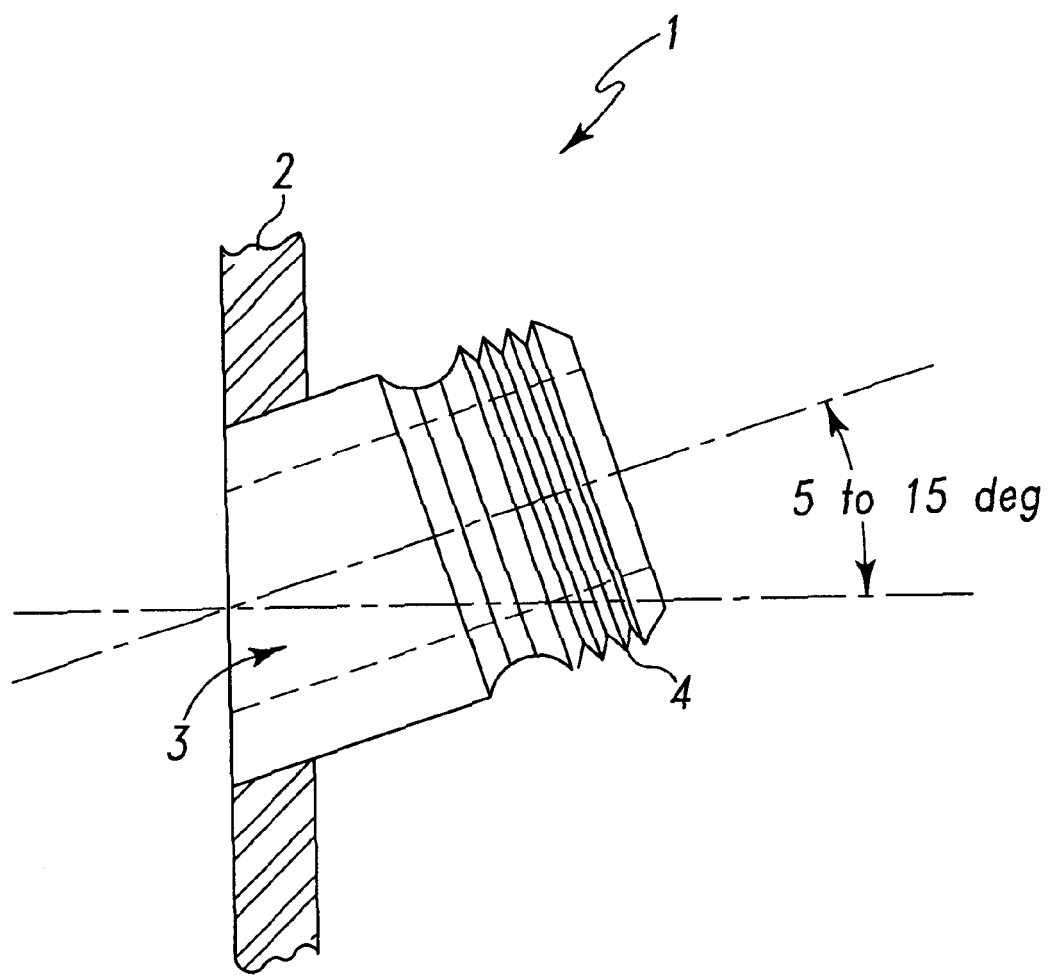
FIG. 1 shows a typical prior art 25 mm weld spud.
Figure 2:
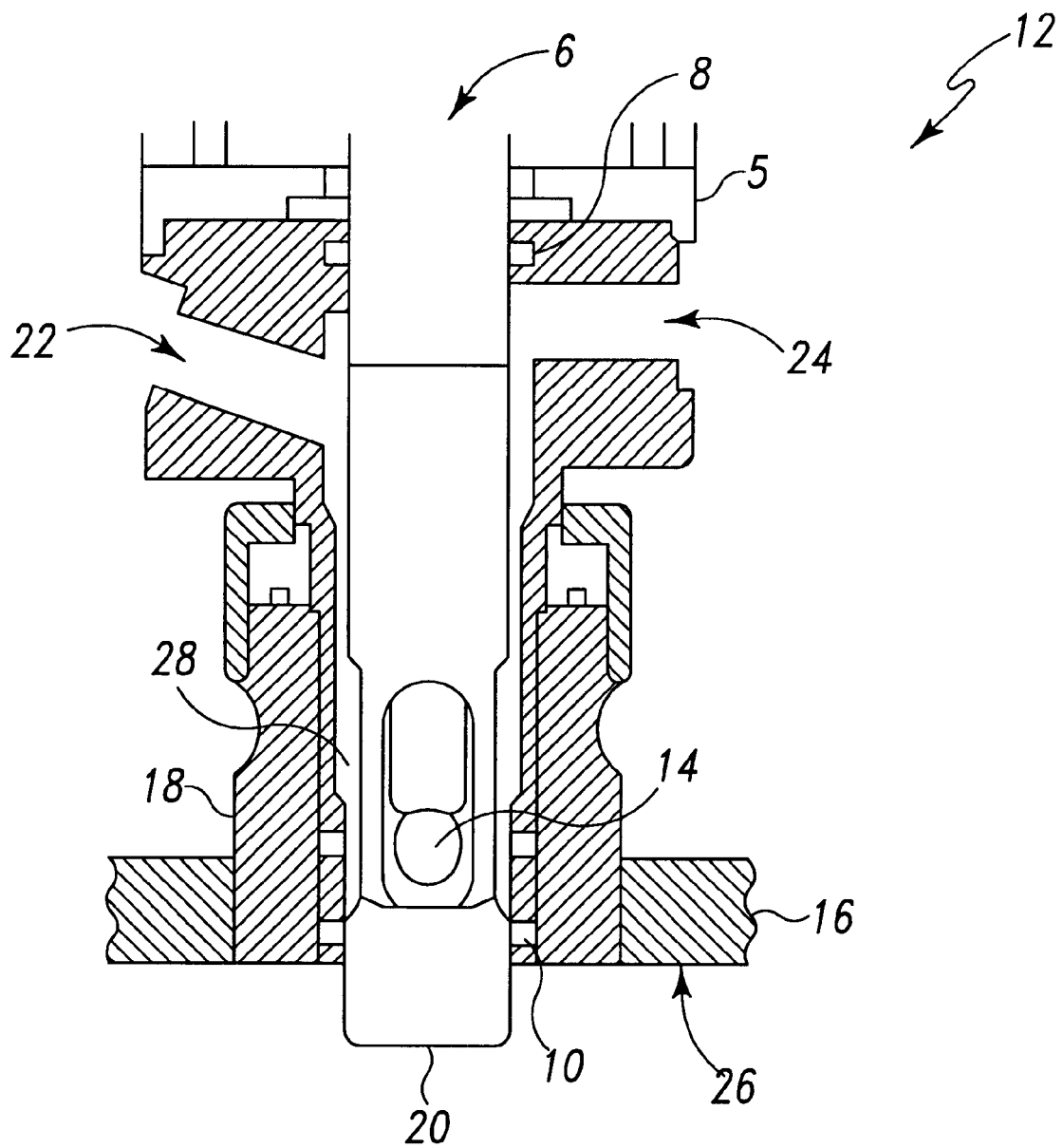
FIG. 2 shows a typical prior art retractable holder in a retracted, cleaning position.
Figure 3:
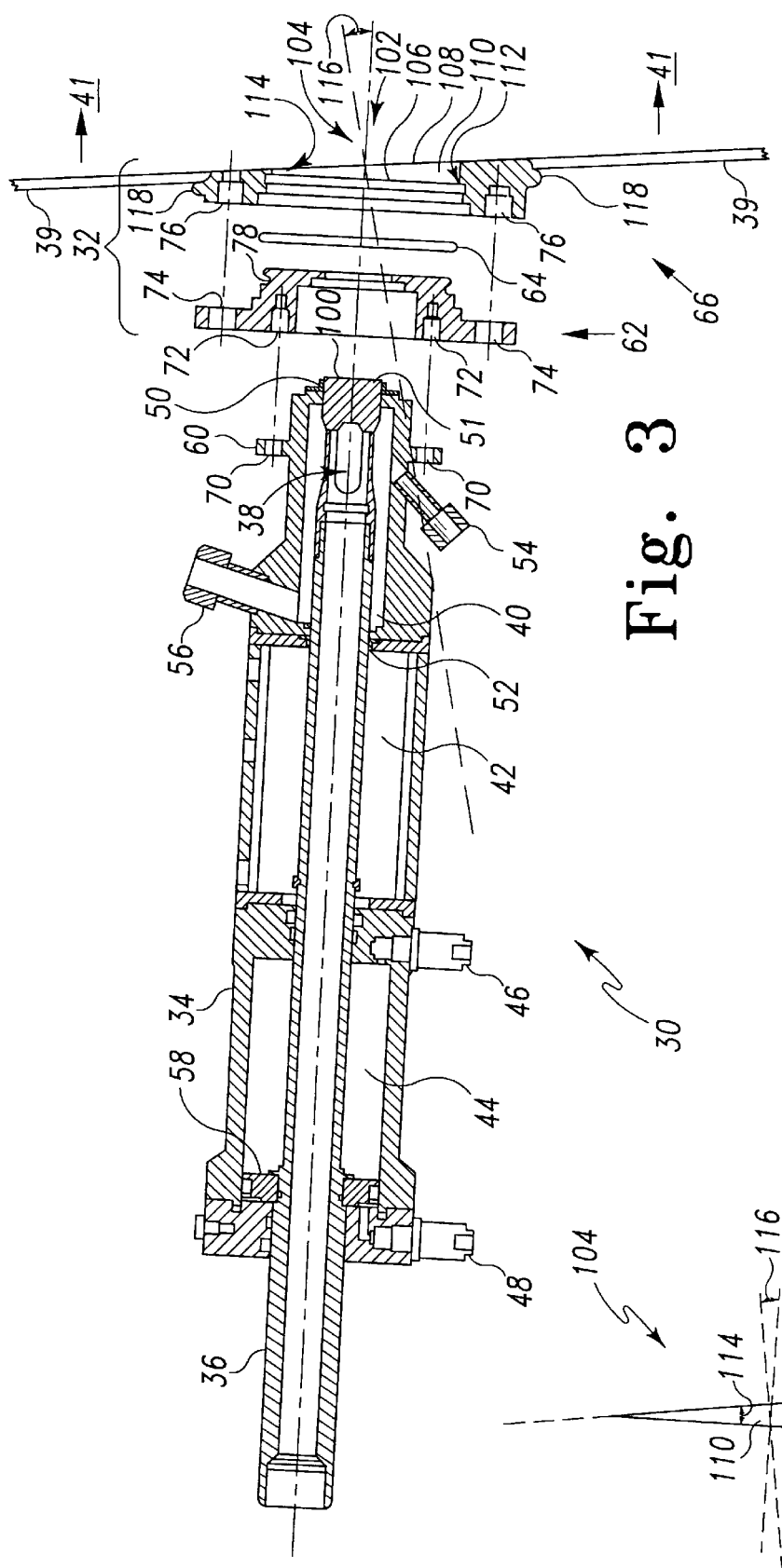
FIG. 3 shows an exploded cross sectional view of a retractable holder and a process connection according to the present invention in a retracted, cleaning position.
Figure 4:
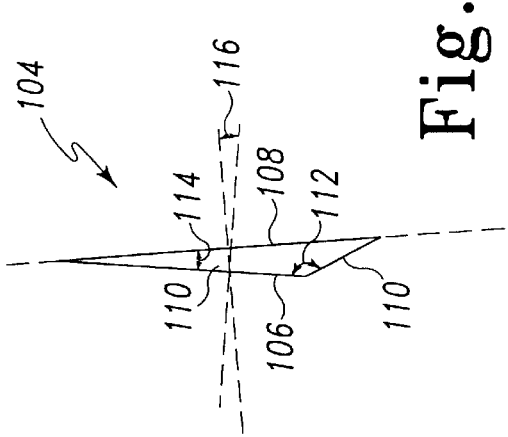
FIG. 4 shows an enlarged view of a tapered flare of an aperture of the process connection of FIG. 3.
Figure 5:
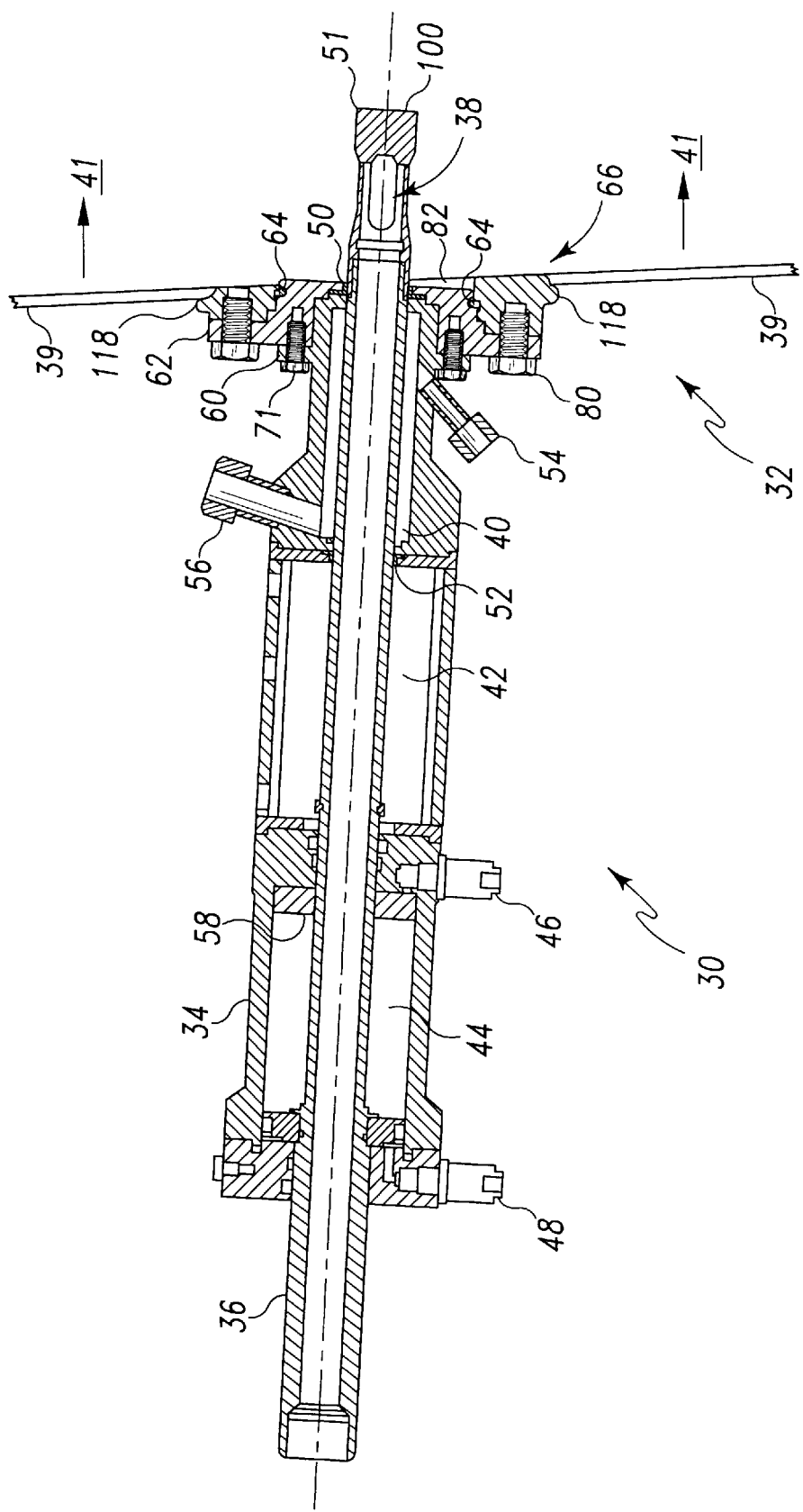
FIG. 5 shows an assembled cross sectional view of the retractable holder and the process connection of FIG. 3 in an extended, measuring position.

FIG. 1 shows a typical prior art 25 mm weld spud 1 which is discussed above in connection with the background of the invention; and FIG. 2 shows a typical prior art retractable holder 12 in a retracted, cleaning position which is discussed above in connection with the background of the invention. FIG. 3 shows an exploded cross sectional view of a retractable holder 30 and a process connection 32 according to the present invention in a retracted, cleaning position; and FIG. 4 shows an enlarged view of a tapered flare 104 of an aperture 102 of the process connection 32 of FIG. 3. FIG. 5 shows an assembled cross sectional view of the retractable holder 30 and the process connection 32 of FIG. 3 in an extended, measuring position. Throughout the figures, like parts are identified by like reference numerals.

As shown in FIGS. 3 and 5, the retractable holder 30 of the present invention includes a cylindrical outer pipe 34, and an inner pipe 36 which is mounted for axial displacement in the outer pipe 34 and which is simultaneously intended to receive a measuring sensor at a sensor chamber 38. The outer pipe 34 sealingly engages the inner pipe 36 (as discussed further below) in a manner to form multiple chambers: a sterilization chamber 40, a separation chamber 42, and a rear pneumatic chamber 44.

The sterilization chamber 40 surrounds the sensor chamber 38. When the retractable holder 30 is in the extended, measuring position (see FIG. 5), the sensor chamber 38 protrudes through the vessel wall 39 into an interior space 41 of the vessel to expose the sensor to the contents of the vessel. When the retractable holder 30 is in the retracted, cleaning position (see FIG. 3) the sensor chamber 38 and the sterilization chamber 40 are separated and isolated from the interior of the vessel. During transition of the inner pipe 36 between the extended and cleaning positions, the interior of the sterilization chamber 40 may be momentarily exposed to the interior of the vessel.

A primary form seal 50 sealingly engages between a front cap 51 of the inner pipe 36 and the outer pipe 34 separating the interior of the sterilization chamber 40 from the interior of the vessel when the retractable holder 30 is in the retracted, cleaning position (see FIGS. 3 and 5). A rear form seal 52 sealingly separates the sterilization chamber 40 from the separation chamber 42 regardless of whether the retractable holder 30 is in the retracted or extended positions. The retractable holder 30 includes a sterilization chamber inlet 54 and a sterilization chamber outlet 56 which can be used for fluid communication with the interior of the sterilization chamber 40.

The separation chamber 42 separates the sterilization chamber from the pneumatic chamber 44. The pneumatic chamber 44 includes a first pressure agent connection 46 and a second pressure agent connection 48. The inner pipe 36 includes a piston-like wider portion 58 which is rigidly connected to the inner pipe 36 and is disposed in the interior of the pneumatic chamber 44 between the first pressure agent connection 46 and the second pressure agent connection 48. By introducing a pressure agent into the first and/or second pressure agent connections 46, 48, the inner pipe 36 can be subjected to the action of the pressure agent for movement of the inner pipe 36 between the extended, measuring position and the retracted, cleaning position. The outer and inner pipes 34 and 36, thereby, form sort of a piston-and-cylinder unit ensuring the axial relative movement of the inner pipe 36, together with the sensor chamber 38, relative to the outer pipe 34. The stroke of the inner pipe 36 in the retractable holder 30 can be designed to be controlled by stops or sensors in the separation chamber 42 and/or the pneumatic chamber 44, or by any other suitable manner.

The process connection 32 includes a mounting flange 62, a process O-ring 64 and a weld spud 66. The retractable holder 30 includes a mounting flange 60 with one or more fastening locations. The mounting flange 62 is configured to attach to the mounting flange 60 of the retractable holder 30, such that, when tightly attached, the primary form seal 50 forms a fluid tight seal between the mounting flange 62 and the retractable holder 30. Each of four holes 70 in the mounting flange 60 are aligned with a respective threaded cavity 72 in the mounting flange 62 and four bolts 71 for attaching the mounting flange 62 to the mounting flange 60. Alternative fastening arrangements for the retractable holder 30 and the mounting flange 62 should be readily apparent to those skilled in the art, one example being threaded studs.

The weld spud 66 is configured to be mounted to the wall of the vessel. The mounting flange 62 is also designed to attach to the weld spud 66, such that, when tightly attached, the process O-ring seal 64 forms a fluid tight seal between the mounting flange 62 and the weld spud 66. The process O-ring 64 is attached to the mounting flange 62 in a depression 78 (see FIG. 3). Each of four holes 74 in the mounting flange 62 are aligned with a respective threaded cavity 76 in the weld spud 66 and four bolts 80 for attaching the mounting flange 62 to the weld spud 66. Alternative fastening arrangements for the mounting flange 62 and the weld spud 66 should be readily apparent to those skilled in the art, one example being threaded studs. The fluid tight seal between the retractable holder 30 and the mounting flange 62, and the fluid tight seal between the mounting flange 62 and the weld spud 66, results in a fluid tight seal between the weld spud 66 and the retractable holder 30.

The process connection 32 is designed to have the prescribed angles, sealing methods and surface finishes to provide what is referred to in the art as "mechanical cleaning" or "clean-in-place." To this end, the process connection 32 defines the aperture 102 which runs through the mounting flange 62 and the weld spud 66 (see FIG. 3). In the exemplary embodiment described herein, the aperture 102 includes the tapered flare 104 having a first rim 106, a second rim 108 that intersects the first rim 106 and is angularly displaced from the first rim 106 by a taper angle 114, and a sidewall 110 that extends between the first rim 106 and the second rim 108, with the sidewall 110 being angularly displaced from the first rim 106 by a flare angle 112 (see FIGS. 3 and 4). When the retractable holder 30 is in the extended, measuring position (see FIG. 5), the measuring sensor extends beyond the first rim 106 into the vessel. When the retractable holder 30 is in the retracted, cleaning position the measuring sensor is separated and isolated from the interior of the vessel and does not extend beyond the first rim 106.

FIG. 4 shows an enlarged view of the tapered flare 104 of the process connection 32. In the exemplary embodiment described herein, it should be appreciated that the taper angle 114 dictates a roughly equivalent mounting angle 116 at which the retractable holder 30, when installed, is oriented with respect to the vessel wall (see also FIG. 3). To comply with the clean-in-place requirements and recommended installation methods for ph electrodes regarding the mounting angle 116, the taper angle 114 is ideally in the range of 5 to 15 degrees, preferably 5 degrees. Further, to meet the clean-in-place requirements regarding prohibitions against acute angles, the flare angle 112 is preferably no less than 135 degrees. To this end, the sidewall 110 is preferably straight (as shown). However, it is noted that the tapered flare 104 as described herein is merely exemplary and in alternative embodiments the tapered flare 104 may include other suitable taper and/or flare angles, may include a suitable concave sidewall or a suitable convex sidewall, or may be configured in any number of other suitable ways to meet the clean-in-place requirements.

Referring to FIGS. 3 and 5, the weld spud 66 also includes a depth stop 118. The depth stop 118 helps properly position the weld spud 66 for welding to the tank in accordance with the clean-in-place requirements. For example, a typical installation requires cutting a round hole into a tank wall, then setting the weld spud 66 into the hole for welding. The diameter of the cut hole is slightly smaller than the diameter of the stop 118 but large enough to allow the weld spud 66 to rest on depth stop 118, so that the weld spud 66 does not fall through the hole but penetrates the hole at an appropriate depth. Accordingly, it should be appreciated that the exact position of the depth stop 118 on the weld spud 66 assumes a standard minimum tank wall thickness. For alternate wall thicknesses, the depth stop 118 may be offset as necessary to ensure flushness of the weld spud 66 with the inside the of the vessel. Additionally, installation may require "weld-bead clean-up;" i.e., grinding and polishing of the weld seam along the inside of the tank, in order to meet the clean-in-place requirements. In any event, it is noted that although the depth stop 118 is preferably a ridge or lip around the weld spud 66, in alternative embodiments the depth stop 118 need not completely surround the weld spud 66.

The retractable holder 30 is designed so that, when the retractable holder 30 is in the retracted, cleaning position, the process wetted moving parts in the sterilization chamber 40 are in complete contact with the fluid introduced through the sterilization chamber inlet 54 and expelled through the sterilization chamber outlet 56. The fluid introduced through the sterilization chamber inlet 54, which may be for cleaning, sterilization, or other purposes, is normally introduced at a high velocity. The cleaning solution impacts the rear face of the front cap 51 in the area of the sensor chamber 38 and then travels axially through the sterilization chamber 40 to the sterilization chamber outlet 56.

The process connection 32 is much shorter than the typical 25 mm port coupling type. This allows the sterilization chamber inlet 54 to be positioned for direct cleaning and/or sterilization of the area directly behind the primary form seal 50 and near the sensor tip in the sensor chamber 38. The cleaning or sterilization agent then moves upwards in a swirling action to exit at the sterilization chamber outlet 56 in a Z-type cleaning path. The measuring probe chamber 38 is in an open lantern design to minimize heat transfer during steam sterilization cycles.

The process connection 32 enables the retractable holder 30 to be attached to a vessel such that, when the retractable holder 30 is in the retracted, cleaning position, the front face 100 of the front cap 51 remains "substantially flush;" i.e., substantially in the same plane as the first rim 106 of the tapered flare 104 or spaced apart from the first rim 106 by a distance not greater than about 3/16 inches. Additionally, the depth stop 118 preferably provides that the second rim 108 of the tapered flair 104 remains "substantially flush" with the interior of the tank wall; i.e., substantially in the same plane as the interior of the tank wall or penetrating the tank wall by a distance of no more than about 1/32 inches. However, it should be appreciated that the distances for the substantially flush mounting of the front face 100 of the front cap 51 with respect to the first rim 106 of the tapered flare 104 and for the substantially flush mounting of the weld spud 66 with respect to the tank wall are merely exemplary, and in alternative embodiments these may be any suitable distances that will not significantly disturb the laminar flow typically required for ideal mixing within these types of vessels in accordance with the clean-in-place requirements.

The foregoing description of the invention is illustrative only, and is not intended to limit the scope of the invention to the precise terms set forth. Although the invention has been described in detail with reference to certain illustrative embodiments, variations and modifications exist within the scope and spirit of the invention as described and defined in the following claims.

What is claimed is:

1. An apparatus for holding a sensor for sensing the contents of a vessel, the vessel having a wall including an interior surface and an opening, the apparatus comprising:

a connector adapted to be coupled to the wall of the vessel, the connector including a first rim, a second rim angularly displaced from the first rim, and a sidewall extending between the first rim and the second rim, the first rim, the second rim, and the sidewall at least partially defining an aperture; and a sensor holder coupled to the sensor and configured to be coupled to the connector, the sensor holder being extendable to position the sensor in an extended position through the aperture of the connector so that the sensor is exposed to the contents and being retractable to position the sensor in a retracted position for cleaning the sensor;

wherein the sidewall is angularly displaced from the first rim by no less than 135 degrees and wherein the second rim is substantially flush with the interior surface of the vessel wall.

2. The apparatus of claim 1, wherein when the sensor is in the extended position, the first portion of the sensor extends beyond the second rim of the aperture into the vessel.

3. The apparatus of claim 2, wherein the first rim is angled relative to the second rim.

4. The apparatus of claim 3, wherein the sensor holder includes a first holder member coupled to the connector and a second holder member coupled to the sensor and closed at one end by a cap having a face facing the wall; the second holder member being moveable relative to the first holder member to position the sensor in the extended position and the retracted position, wherein when the sensor is in the retracted position, the face of the cap is substantially in the same plane as the first rim.

5. The apparatus of claim 4, wherein when the sensor is in the retracted position, the face of the cap is spaced apart from the first rim by no more than 3/16 inches.

6. The apparatus of claim 4, wherein the connector includes a first connector member adapted to be coupled to the wall of the vessel, the first connector member including the first rim and the second rim.

7. The apparatus of claim 6, wherein the connector further includes a second connector member coupled to the sensor holder and coupled to the first connector member and a fluid tight seal interposed between the first connector member and the second connector member.

8. The apparatus of claim 7, wherein the angle between the first rim and the second rim is not less than 5 degrees and not more than 15 degrees.

9. The apparatus of claim 8, wherein the sidewall is generally flat between the first rim and the second rim.

10. An apparatus for connecting a sensor holder, the sensor holder being coupled to a sensor, to an opening in a wall of a vessel, the vessel wall having an interior surface, the apparatus comprising:

a connector adapted to be coupled to the sensor holder and further adapted to be coupled to the wall of the vessel, the connector defining an aperture including a first rim, a second rim angularly displaced from the first rim, and a sidewall extending between the first rim and the second rim;

wherein the sidewall is angularly displaced from the first rim by no less than 135 degrees and the second rim is substantially flush with the interior surface of the vessel wall, the sensor holder being extendable to position the sensor in an extended position so that the sensor is exposed to the contents of the vessel and being retractable to position the sensor in a retracted position for cleaning the sensor.

11. The apparatus of claim 10, wherein the connector includes a first member configured to be attached to the wall of the vessel, the first member including the first rim and the second rim.

12. The apparatus of claim 11, wherein the connector further includes a second member coupled to the first member and a fluid tight seal interposed between the first member and the second member.

13. The apparatus of claim 12, wherein the sidewall is generally flat between the first rim and the second rim.

14. The apparatus of claim 13, wherein the second rim is angularly displaced from the first rim by not less than 5 degrees and not more than 15 degrees.

15. The apparatus of claim 13, wherein the first rim is angled relative to the second rim.

16. The apparatus of claim 1 wherein the second rim is spaced apart from the interior vessel wall by up to about 1/32 inches.

17. The apparatus of claim 1 wherein the connector further includes a depth stop configured to locate the second rim of the connector substantially flush to the interior vessel wall.

18. The apparatus of claim 10 wherein the second rim is spaced apart from the interior vessel wall by up to about 1/32 inches.

19. The apparatus of claim 10 wherein the connector further includes a depth stop configured to locate the second rim of the connector substantially flush to the interior vessel wall.

* * * * *

UNITED STATES PATENT AND TRADEMARK OFFICE
CERTIFICATE OF CORRECTION

PATENT NO. : 6,773,678 B2
DATED : August 10, 2004
INVENTOR(S) : Cummings et al.

It is certified that error appears in the above-identified patent and that said Letters Patent is hereby corrected as shown below:

<u>Title page,</u>
Item [56], References Cited, FOREIGN PATENT DOCUMENTS, change
"EP 067211 12/1995" to -- EP 0687211 12/1995 --

Signed and Sealed this

Fifth Day of October, 2004

JON W. DUDAS
*Director of the United States Patent and Trademark Office*